United States Patent [19]

Arita et al.

[11] Patent Number: 5,522,263

[45] Date of Patent: Jun. 4, 1996

[54] APPARATUS AND METHOD FOR INSPECTING SOLDERING CONDITION OF ELECTRONIC COMPONENT BY USING ULTRASONIC OSCILLATION

[75] Inventors: Kiyoshi Arita; Kouichi Takahashi, both of Fukuoka-ken, Japan

[73] Assignee: Matsushita Electric Industrial Co., Ltd., Osaka, Japan

[21] Appl. No.: 426,786

[22] Filed: Apr. 21, 1995

[30] Foreign Application Priority Data

Apr. 25, 1994 [JP] Japan .................................. 6-086668

[51] Int. Cl.⁶ ............................................... G01B 17/00
[52] U.S. Cl. ................................................. 73/588; 73/602
[58] Field of Search ..................... 364/508, 552, 364/506, 507, 550; 73/577, 582, 588, 598, 600, 602

[56] References Cited

U.S. PATENT DOCUMENTS 4,218,922 8/1980 Ensminger ............................ 73/588
5,170,929 12/1992 Long .................................... 73/588
5,291,419 3/1994 Satoh ................................. 364/508

FOREIGN PATENT DOCUMENTS 4199725 7/1992 Japan .

Primary Examiner—Hezron E. Williams
Assistant Examiner—Christine K. Oda
Attorney, Agent, or Firm—Pollock, Vande Sande & Priddy

[57] ABSTRACT

A measuring device 40 measures an ultrasonic waveform provided to an inspection tool 1. A target energy memory section 45 memorizes a target energy consumed by the inspection tool 1 when the inspection tool 1 is depressed on the soldered portion of an electronic component which is properly soldered on a substrate. A reference waveform memory section 44 memorizes a reference waveform corresponding to an ultrasonic waveform measured in a no load condition of the inspection tool 1. A CPU 43 makes a judgement on whether the soldering condition of the soldered portion of the electronic component is acceptable or not based on a difference between the reference waveform and the waveform measured by the measuring device 40.

16 Claims, 5 Drawing Sheets

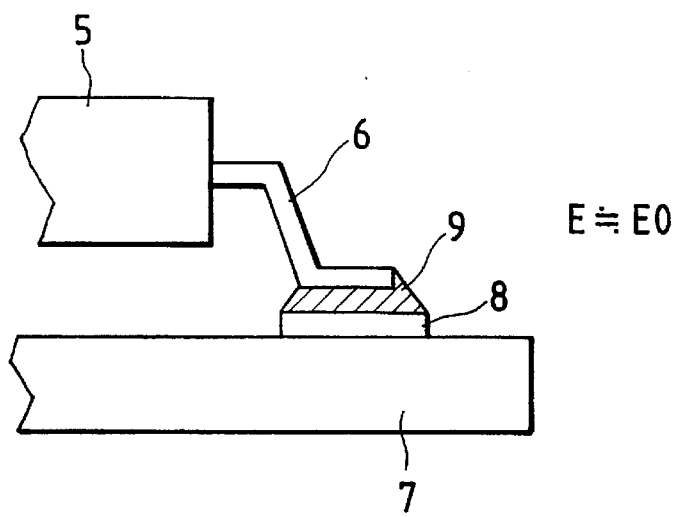
FIG. 4A  $E \fallingdotseq E0$
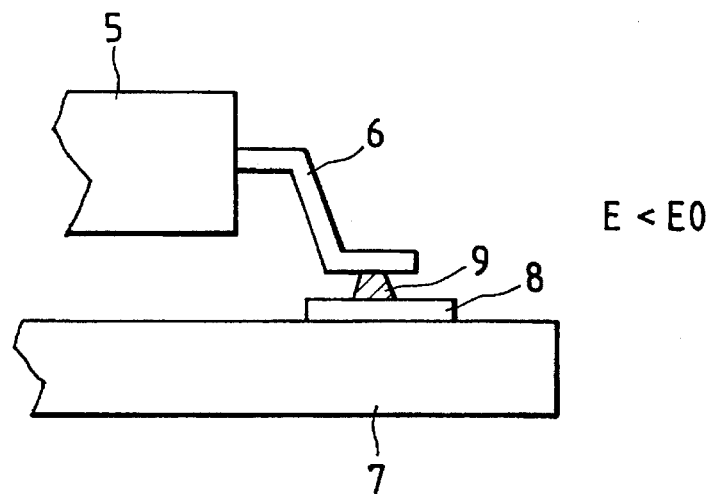
FIG. 4B  $E < E0$
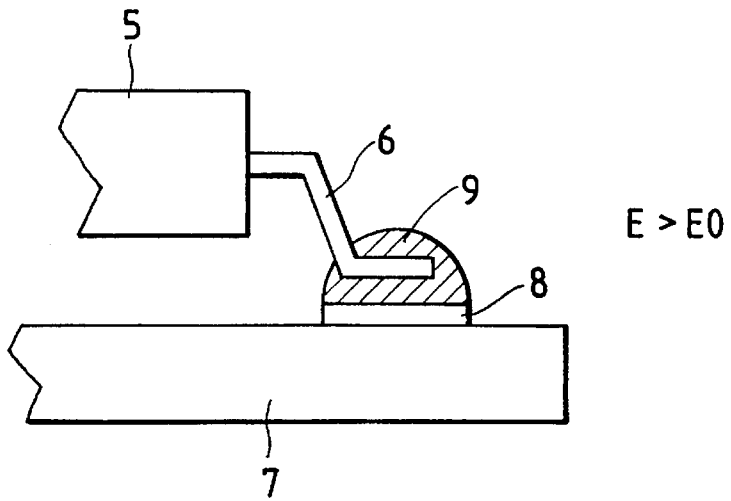
FIG. 4C  $E > E0$

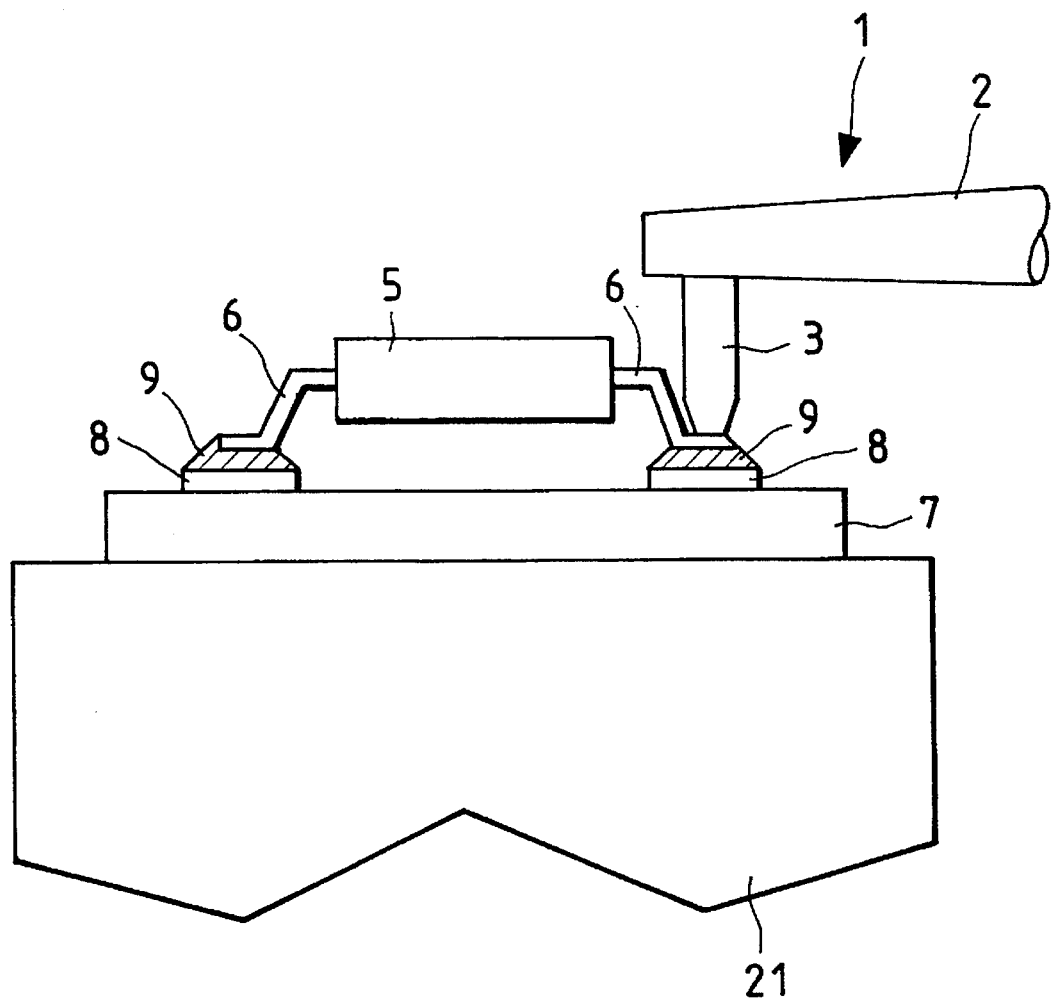

APPARATUS AND METHOD FOR INSPECTING SOLDERING CONDITION OF ELECTRONIC COMPONENT BY USING ULTRASONIC OSCILLATION

BACKGROUND OF THE INVENTION

1. Field of the Invention

This invention relates to an apparatus and a method for inspecting soldering condition of an inspected object, such as an electronic component soldered onto a substrate, and more particularly to an apparatus and a method for judging whether the soldering condition of the inspection object is acceptable on the basis of energy consumed by an inspection tool during the inspection where the inspection tool is depressed against a soldered portion of the inspection object and is subjected to high-frequency oscillation such as ultrasonic oscillation.

2. Prior Art

As a method of making a judgement whether a soldered portion of an electronic component on a substrate is acceptable or not, there is known a method of applying ultrasonic oscillation to the soldered portion to be inspected. FIG. 6 shows a side view showing a part of a soldering condition inspecting apparatus which is conventionally available. In the drawing, a depressing-type inspection tool 1 comprises a pin-like inspection piece 3 fixed to the distal end of a horn 2. This inspection tool 1 is substantially identical to a bonding tool used for an inner lead bonding apparatus disclosed, for example, in the Unexamined Japanese Patent application No. 4-199725/1992. An electronic component 5 has a plurality of leads 6—6 extending outward from the side surfaces thereof. Each of these leads 6— 6 is bent downward and is soldered at its lower end onto an electrode 8 of a substrate 7 by solder 9. A base 21 mounts the substrate 7 thereon.

The inspection of soldering condition is carried out in the following manner. The horn 2 is subjected to ultrasonic oscillation generated by an appropriate ultrasonic oscillation means (not shown) which normally comprises an ultrasonic oscillator, a step-up transformer, and a piezoelectric element. Then, the lower end of inspection piece 3 is depressed on the upper surface of the lead 6, and provided an amplitude of a waveform of an ultrasonic current obtained to the inspection tool 1 by the ultrasonic oscillation means. The amplitude thus obtained is used to make a judgement on whether the soldering condition of the inspected component (i.e. the electronic component 5) is acceptable. In other words, this method is characterized in that the soldering condition is judged based on the correlation between bonding strength of the soldered portion and the amplitude of ultrasonic current of the ultrasonic oscillation means.

However, the value of an ultrasonic current is adversely affected by numerous factors, such as fluctuation of impedance of the inspection tool 1 and mechanical errors of the apparatus. In other words, these factors become the causes of measuring errors. Hence, accuracy cannot be assured in the judgement of the soldering condition; thus there may be errors in the judgement. It is believed that such fluctuation of impedance or mechanical errors chiefly result from the connecting rigidity between the horn 2 and the inspection piece 3 (namely, whether the connection of the inspection piece 3 to the horn 2 is rigid or soft) or scattering of sizes and materials of the horn 2 and the inspection piece 3. In this connection, the conventional method requires re-check of the characteristics of the ultrasonic current every time parts of the inspection piece 3 are exchanged, in order to newly set the judgement standard of the soldering condition. It therefore requires a great amount of manpower.

SUMMARY OF THE INVENTION

Accordingly, in view of above-described problems encountered in the prior art, a principal object of the present invention is to provide an apparatus and a method for inspecting soldering condition of an inspected object capable of accurately judging whether the soldering condition is good or bad using an inspection tool subjected to vibration by high-frequency oscillation. More specifically, the inventors of the present invention have found the fact that the bonding strength of a soldered portion has more relevant correlation with the consumption energy of the inspection tool than the amplitude of the ultrasonic current. Accordingly, the present invention provides an apparatus and a method for judging whether the soldering condition is acceptable or not on the basis of energy consumed by the inspection tool when the inspection piece of the inspection tool is depressed against the soldered portion of the inspected object while the inspection tool is subjected to high-frequency oscillation such as ultrasonic oscillation.

In order to accomplish this and other related objects, a first aspect of the present invention provides a soldering condition inspecting apparatus comprising: an inspection tool; oscillation means for causing the inspection tool to vibrate; memory means for memorizing a target value used as a reference value for judging soldering condition of a soldered portion of an inspected object; consumption energy calculating means for calculating the actual energy consumed by the inspection tool when the inspection tool is depressed against the soldered portion of the inspected object under vibration generated by the oscillation means for a predetermined time; and judging means for making a judgement on whether the soldering condition of the soldered portion of the inspected object is acceptable or not by comparing the actually consumed energy calculated by the consumption energy calculating means with the target value memorized in the memory means.

More specifically, the present invention provides a soldering condition inspecting apparatus comprising: an inspection tool; oscillation means for causing the inspection tool to vibrate; measuring means for measuring an ultrasonic waveform given to the inspection tool; target value memory means for memorizing a target value used as a reference value for judging soldering condition of a soldered portion of an inspected object; reference waveform memory means for memorizing a reference waveform which represents a waveform obtainable when the inspection tool is vibrated under a predetermined reference condition; consumption energy calculating means for calculating the actual energy consumed by the inspection tool when the inspection tool is depressed against the soldered portion of the inspected object under vibration generated by the oscillation means for a predetermined time, the actually consumed energy being obtained based on a difference between the reference waveform and a waveform measured when the inspection tool is depressed against the soldered portion of the inspected object; and judging means for making a judgement on whether the soldering condition of the soldered portion of the inspected object is acceptable or not by comparing the actually consumed energy calculated by the consumption energy calculating means with the target value memorized in the target value memory means.

In the above soldering condition inspecting apparatus of the present invention, it is preferable that the oscillation means causes ultrasonic vibration, and the target value memorized in the target value memory means is an energy to be consumed by the inspection tool when the soldered portion of the inspected object is in a predetermined proper soldering condition, while the inspection tool is subjected to vibration generated by the oscillation means for a predetermined time.

Furthermore, the measuring means comprises first and second detecting means for obtaining values representing an effective voltage V and an effective current I of the oscillation means. These first and second detecting means are connected to multiplication means, wherein a product of the effective voltage V and effective current I is obtained. The multiplication means is connected to latch means for temporarily holding the product V×I entered from the multiplication means. The product V×I is entered into the consumption energy calculating means. The soldering condition inspecting apparatus further comprises judgement result memory means for memorizing the judging result of the soldering condition in the judging means, and also comprises control means for actuating the oscillation means in accordance with data stored in the judgement result memory means. Moreover, the inspection tool is a depressing-type inspection tool comprising a pin-like inspection piece fixed to a distal end of a horn. The horn is vibrated by the oscillation means, while a lower end of the inspection piece is depressed on the soldered portion of the inspected object.

Still further, a second aspect of the present invention provides a soldering condition inspecting method comprising steps of: memorizing a reference waveform into a reference waveform memory means, the reference waveform representing a waveform obtainable when inspection tool is vibrated by oscillation means under a predetermined reference condition; calculating the actual energy consumed by the inspection tool based on a difference between the reference waveform and a waveform measured when the inspection tool is depressed against a soldered portion of an inspected object under vibration generated by oscillation means; and making a judgement on whether the soldering condition of the soldered portion of the inspected object is acceptable or not by comparing the actually consumed energy calculated in the calculating step with a target value. The target value is an energy to be consumed by the inspection tool when the soldered portion of the inspected object is in a predetermined proper soldering condition, while the inspection tool is subjected to vibration generated by the oscillation means for a predetermined time.

In accordance with the above-described apparatus and method of the present invention, it becomes possible to accurately inspect the soldering condition of an inspected object by calculating an actually consumed energy by the inspection tool when it is depressed on the soldered portion of the inspected object under high-frequency oscillation.

BRIEF DESCRIPTION OF THE DRAWINGS

The above and other objects, features and advantages of the present invention will become more apparent from the following detailed description which is to be read in conjunction with the accompanying drawings, in which:

FIGS. 4A–4C are partial side views respectively showing a typical soldering condition between a lead of an electronic component and an electrode of a substrate;

FIG. 6 is a side view showing a part of a conventionally available soldering condition inspecting apparatus.

DETAILED DESCRIPTION OF THE PREFERRED EMBODIMENT

Figure 1:
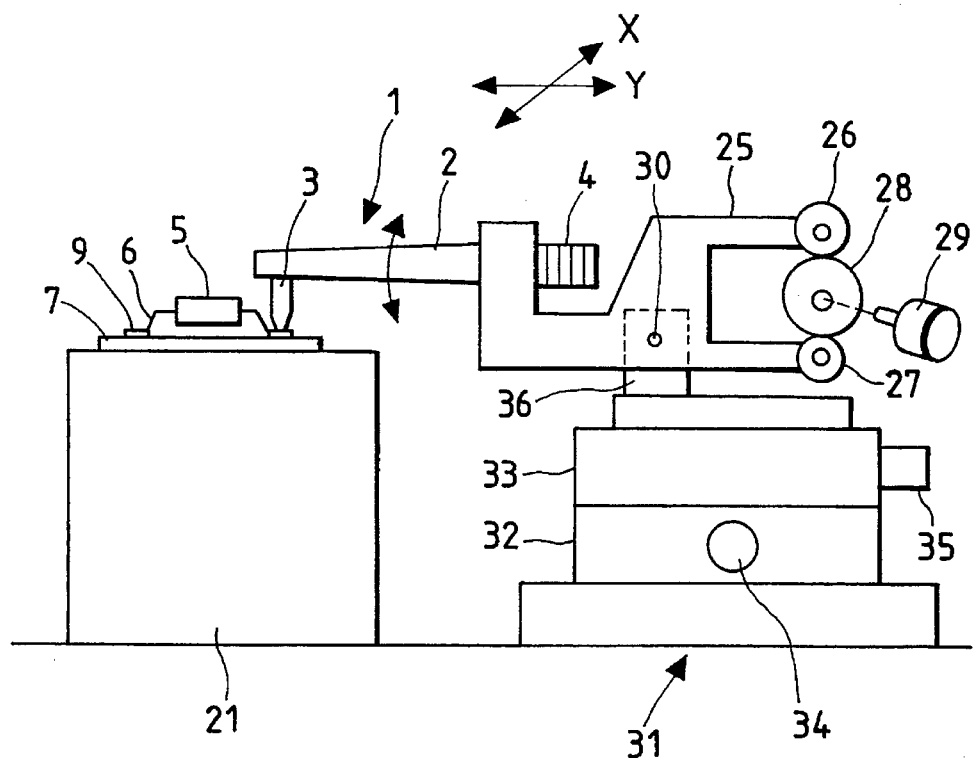
FIG. 1 is a side view showing a soldering condition inspecting apparatus in accordance with one embodiment of the present invention.

A preferred embodiment of the present invention will be explained in greater detail hereinafter, with reference to the accompanying drawings. Identical parts are denoted by identical reference numerals throughout the views. A soldering condition inspecting apparatus shown in FIGS. 1 and 2 fundamentally comprises the components disclosed in FIG. 6. In the drawings, a depressing-type inspection tool 1 comprises a pin-like inspection piece 3 fixed to the distal end of a horn 2. An electronic component 5 has a plurality of leads 6—6 extending outward from the side surfaces thereof. Each of these leads 6—6 is bent downward and is soldered at its lower end onto an electrode 8 of a substrate 7 by solder 9. A base 21 mounts the substrate 7 thereon.

A base end of the horn 2 is supported on the front end of a frame 25. A pair of cam followers 26 and 27 is rotatably provided at the rear end of the frame 25. A cam 28 is sandwiched between the cam followers 26 and 27. A motor 29 rotates the cam 28. The frame 25 swings about a pin 30 in an up-and-down direction. The horn 2 swings in the same direction, as shown by an arrow in the drawing. The inspection piece 3 is depressed on the lead 6. A table unit 31 includes an X table 32 and a Y table 33 piled up in the up-and-down direction. The frame 25 is supported on a bearing 36 provided on the Y table 33. When a drive motor 34 of the X table 32 and a drive motor 35 of the Y table 33 are driven, the frame 25 and the horn 2 held on the frame 25 are moved together in both the X- and Y-directions, i.e. along the horizontal plane. The inspection piece 3 is positioned at a predetermined inspection position.

Figure 2:
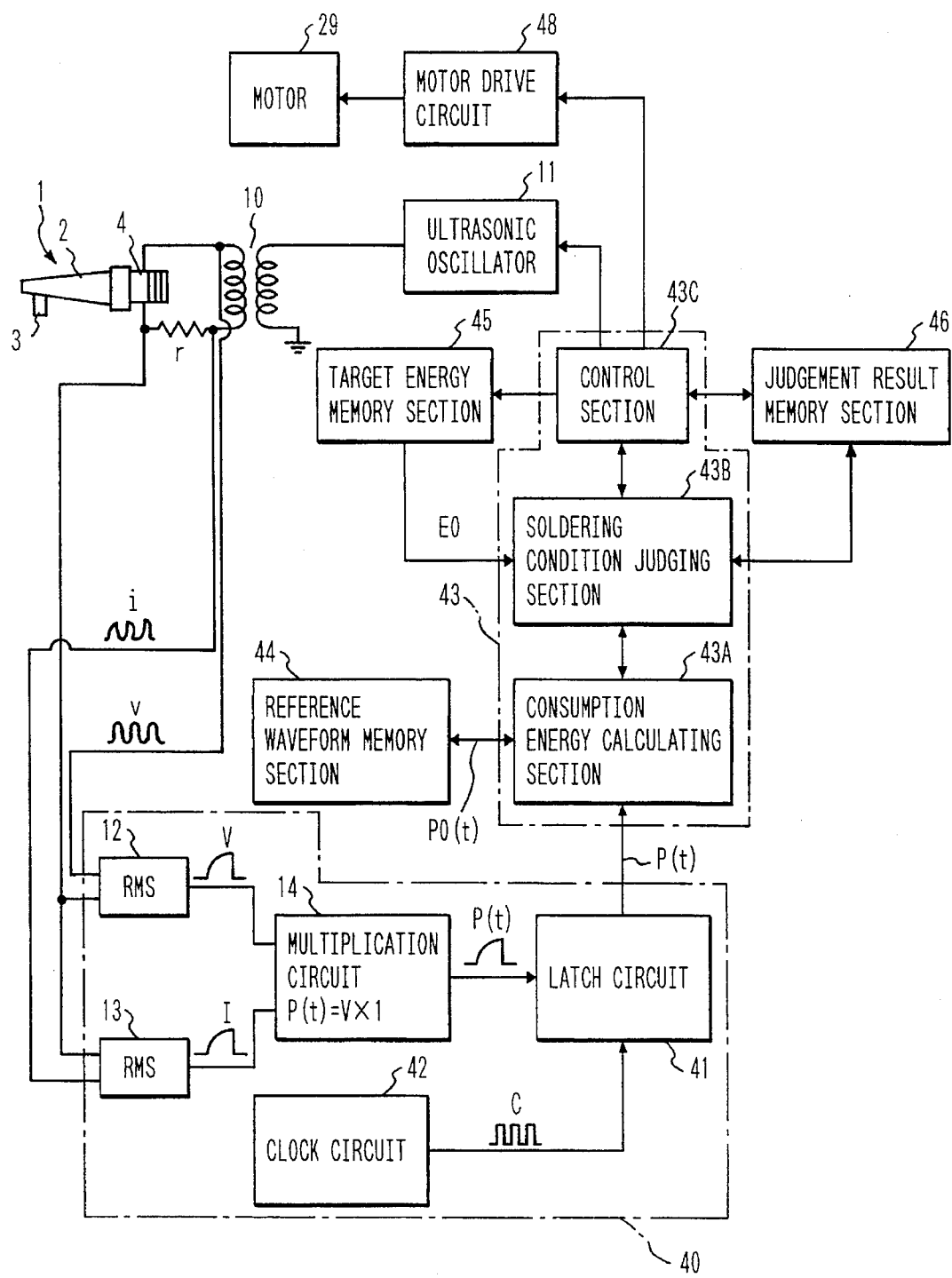
FIG. 2 is a block diagram showing an ultrasonic oscillation apparatus incorporated in the soldering condition inspecting apparatus in accordance with the one embodiment of the present invention.

Next, an ultrasonic oscillation device will be explained with reference to FIG. 2.. A first effective value transformation circuit (1st RMS) 12 and a second effective value transformation circuit (2nd RMS) 13 are connected to a multiplication circuit 14. The multiplication circuit 14 is connected to a latch circuit 41. The first RMS 12 transforms a secondary voltage v of the transformer 10 into an effective value voltage V, while the second RMS 13 transforms a secondary voltage i of the transformer 10 into an effective value current I. A clock circuit 42 supplies a clock signal c to the latch circuit 41. The latch circuit 41 temporarily holds an ultrasonic power P(t)=V×I (J/S) entered from the multiplication circuit 14 in response to the clock signal c supplied from the clock circuit 42, and then supplies this ultrasonic power P(t) to a consumption energy calculation section 43A. The first RMS 12, the second RMS 13, the multiplication circuit 14, the latch circuit 41 and the clock circuit 42 cooperatively constitute a measuring means 40 for measuring an ultrasonic waveform given to the inspection tool 1.

A reference waveform memory section 44, memorizing a reference waveform, supplies the consumption energy calculation section 43A with a reference waveform of an ultrasonic power P0(t) representing an ultrasonic power measured when the inspection tool 1 is in a predetermined reference condition. A target energy memory section (target value memory section) 45, memorizing a target energy (target value) E0(J) used as a reference value for the judgement of soldering condition, enters its data into a soldering condition judging section 43B. The consumption energy calculation section 43A obtains a consumed energy E representing an actually consumed ultrasonic energy on the basis of a difference between the reference waveform of the ultrasonic power P0(t) and a waveform of an ultrasonic power P(t) which is actually measured when the inspection tool 1 is depressed on the soldered portion of the inspection object under ultrasonic oscillation. The soldering condition judging section 43B makes a judgement as to whether or not the soldering condition is acceptable by comparing the target energy E0 and the consumed energy E. Details of the reference waveform and the target energy will be explained later with reference to the graph of FIG. 3. A judgement result memory section 46 memorizes the judgement result of the soldering condition obtained in the soldering condition judging section 43B. A control section 43C supplies the target energy memory section 45 with a target energy, reads the data memorized in the judgement result memory section 46, and controls an ultrasonic oscillator 11 and a motor drive circuit 48 which actuates the motor 29. The consumption energy calculation section 43A, the soldering condition judging section 43B and the control section 43C are constituted by a CPU 43.

Figure 3:
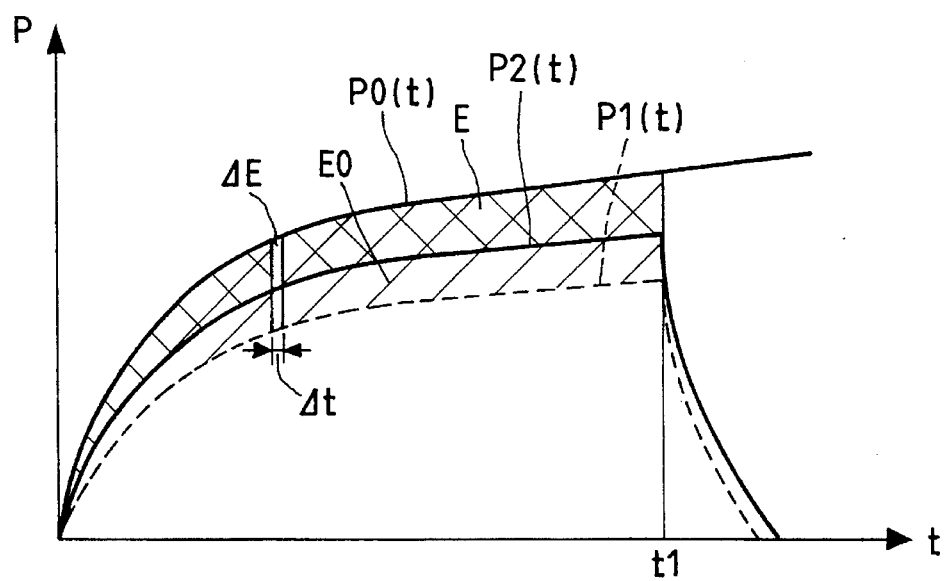
FIG. 3 is a graph showing ultrasonic waveforms measured by the soldering condition inspecting apparatus in accordance with the one embodiment of the present invention.

FIG. 3 shows ultrasonic waveforms. In the drawing, P0(t) represents an ultrasonic power in the no load condition where the inspection piece 3 is spaced off the lead 6. In this invention, the waveform of this ultrasonic power P0(t) is referred to as a reference waveform and is stored beforehand in the reference waveform memory section 44. The reference waveform of the ultrasonic power P0(t) can be simply obtained by rendering the inspection tool 1 operate in the no load condition. This reference waveform should be measured when the impedance of the inspection tool 1 is changed. For example, the impedance may change when the inspection piece 3 is exchanged or at the beginning of a daily operation of the apparatus. The newly measured reference waveform is re-registered in the target energy memory section 45.

In FIG. 3, P1(t) represents an ultrasonic power to be obtained when the lead 6 is correctly and firmly soldered on the electrode 8. The bonding strength of the soldered portion 9 has an interrelation with an energy E0 corresponding to an area difference between the reference waveform of the ultrasonic power P0(t) and the waveform of the ultrasonic power P1(t). This energy E0 is an above-described target energy, which is expressed by right-ascending hatching lines in the drawing. The target energy E0 is referred to as a setting energy.

In FIG. 3, P2(t) is an ultrasonic power measured when the soldering condition of the lead 6 is not acceptable and therefore the lead 6 is not firmly soldered onto the electrode 8. The consumed energy E is obtained as an area difference between the reference waveform of the ultrasonic power P0(t) and the waveform of the ultrasonic power P2(t), which is expressed by right-descending hatching lines in the drawing. In view of the above, there is provided an adequate measuring time t1 to obtain a consumed energy E. When the consumed energy E is closer to the setting energy (i.e. target energy) E0, it is considered that the soldering condition is acceptable. When the difference between the consumed energy E and the setting energy E0 is significantly large, it is considered that the soldering condition is unsatisfactory.

FIGS. 4A, 4B and 4C show typical examples of the soldering condition. When the soldering condition is normal (acceptable) as shown in FIG. 4A, the consumed energy is substantially identical with the setting energy (i.e. E≈E0). When the bonding strength is much too small due to lack of solder as shown in FIG. 4B, the consumed energy is smaller than the setting energy (i.e. E<E0). On the contrary, when the bonding strength is much too large due to surplus of solder as shown in FIG. 4C, the consumed energy is larger than the setting energy (i.e. E>E0).

Figure 5:
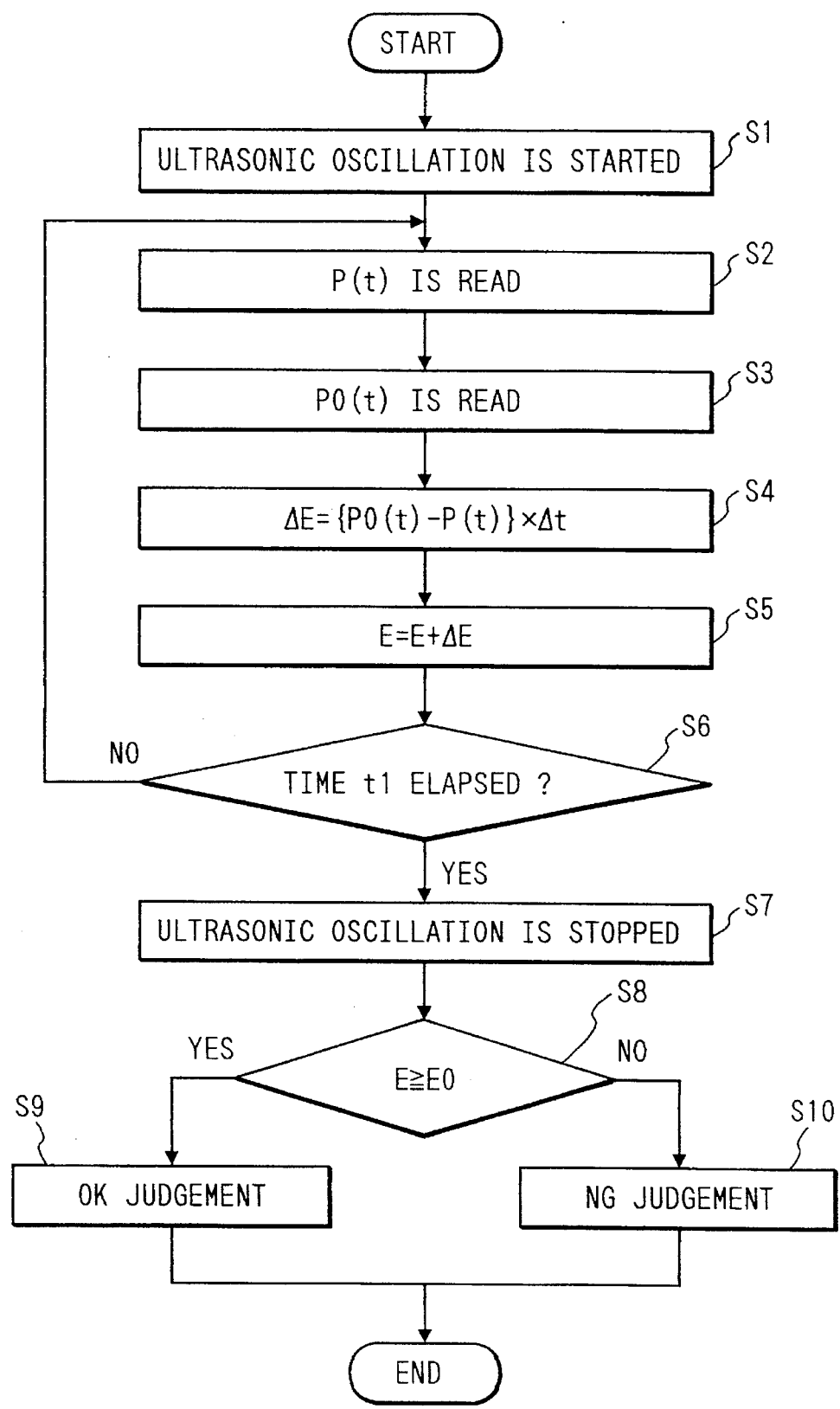
FIG. 5 is a flow chart showing operation of soldering condition judgement of the soldering condition inspecting apparatus in accordance with one embodiment of the present invention.

An operation of the above-described soldering condition inspecting apparatus will be explained in greater detail with reference to the flow chart of FIG. 5, this operation being executed by the CPU 43. In a step S1, the control unit 43C generates a command of starting an ultrasonic oscillation. More specifically, the inspection tool 1 is subjected to ultrasonic oscillation, and the inspection piece 3 is depressed on the lead 6. The multiplication circuit 14 generates the ultrasonic power P(t), i.e. V×I, which is entered into the latch circuit 41. In a step S2, the consumption energy calculation section 43A reads the value of the ultrasonic power P(t) memorized in the latch circuit 41. Next, in a step S3, the consumption energy calculation section 43A reads the ultrasonic power P0(t) memorized beforehand in the reference waveform memory section 44. Subsequently, the consumption energy calculation section 43A calculates an energy difference $\Delta E$ between the ultrasonic powers P0(t) and P(t), i.e. $\Delta E = \{P0(t) - P(t)\} \times \Delta t$. As shown in FIG. 3, $\Delta t$ is a tiny time interval, while $\Delta E$ is an area difference between the ultrasonic powers P0(t) and P(t) corresponding to this time interval $\Delta t$. In a step S5, the energy difference $\Delta E$ is successively accumulated to obtain a total amount of the consumed energy E. Then, in a step S6, it is judged whether the predetermined measuring time t1 has elapsed. If the time t1 has not yet elapsed, the flow returns to the step S2. On the other hand, if the time t1 has already elapsed, the flow proceeds to a step S7 to cause the control section 43C to stop the ultrasonic oscillation. Thereafter, it is judged in a step S8 whether the consumed energy E thus measured is not smaller than the setting energy E0. If the judgement results in YES in the step S8, it is considered that the soldering condition is OK (acceptable). On the contrary, if the judgement results in NO in the step S8, it is considered that the soldering condition is NG (unsatisfactory). This judgement result is memorized in the judgement result memory section 46.

Although the present embodiment adopts the formula $E \geq E0$ as a judgement condition in the step S8, this formula can be replaced by any other adequate expression in view of possible measuring errors and tolerance errors, or occurrence of the FIG. 4C soldering condition which has a surplus bonding strength. For example, the formula $E \geq E0$ of the step S8 can be replaced by the following formula.

$$E0 - \delta E \leq E \leq E0 + \delta E$$

where $\delta E$ is an allowable error.

Moreover, although the present invention defines the reference condition as a no load condition, it is needless to say that the reference condition can be any other condition with a specific imparted load.

As explained in the foregoing description, the present invention assures accuracy in the detection of the soldering condition, since an actual consumed energy by the inspection tool is obtained when it is depressed on the soldered portion of the inspected object, the obtained data then being compared with the predetermined reference value to judge the soldering condition. Hence, even if the impedance of the inspection tool is varied, all that to be required is to measure a reference waveform, which is fairly simple compared with the conventional method which required setting of a new reference value for the judgement taking account of numerous and complicated factors. It is very advantageous in management of operation..

As this invention may be embodied in several forms without departing from the spirit of essential characteristics thereof, the present embodiment as described is therefore intended to be only illustrative and not restrictive, since the scope of the invention is defined by the appended claims rather than by the description preceding them, and all changes that fall within metes and bounds of the claims, or equivalents of such metes and bounds, are therefore intended to be embraced by the claims.

What is claimed is:

1. A soldering condition inspecting apparatus comprising:

an inspection tool;

oscillation means for causing said inspection tool to vibrate;

memory means for memorizing a target value used as a reference value for judging soldering condition of a soldered portion of an inspected object;

consumption energy calculating means for calculating an actual energy consumed by said inspection tool when said inspection tool is depressed against said soldered portion of the inspected object under vibration generated by said oscillation means for a predetermined time; and judging means for making a judgement on whether the soldering condition of the soldered portion of the inspected object is acceptable by comparing the actually consumed energy calculated by said consumption energy calculating means with said target value memorized in said memory means.

2. The soldering condition inspecting apparatus defined by claim 1, wherein said oscillation means causes ultrasonic vibration.

3. The soldering condition inspecting apparatus defined by claim 1, wherein said target value memorized in said memory means is an energy to be consumed by the inspection tool when the soldered portion of the inspected object is in a predetermined proper soldering condition, while said inspection tool is subjected to vibration generated by said oscillation means for a predetermined time.

4. A soldering condition inspecting apparatus comprising:

an inspection tool;

oscillation means for causing said inspection tool to vibrate;

measuring means for measuring an ultrasonic waveform given to said inspection tool;

target value memory means for memorizing a target value used as a reference value for judging soldering condition of a soldered portion of an inspected object;

reference waveform memory means for memorizing a reference waveform which represents a waveform obtainable when said inspection tool is vibrated under a predetermined reference condition;

consumption energy calculating means for calculating an actual energy consumed by said inspection tool when said inspection tool is depressed against said soldered portion of the inspected object under vibration generated by said oscillation means for a predetermined time, said actually consumed energy being obtained based on a difference between said reference waveform and a waveform measured when said inspection tool is depressed against the soldered portion of the inspected object; and judging means for making a judgement on whether the soldering condition of the soldered portion of the inspected object is acceptable by comparing the actually consumed energy calculated by said consumption energy calculating means with said target value memorized in said target value memory means.

5. The soldering condition inspecting apparatus defined by claim 4, wherein said oscillation means causes ultrasonic vibration.

6. The soldering condition inspecting apparatus defined by claim 4, wherein said target value memorized in said target value memory means is an energy to be consumed by the inspection tool when the soldered portion of the inspected object is in a predetermined proper soldering condition, while said inspection tool is subjected to vibration generated by said oscillation means for a predetermined time.

7. The soldering condition inspecting apparatus defined by claim 4, wherein said measuring means comprises first and second detecting means for obtaining values representing an effective voltage V and an effective current I of said oscillation means.

8. The soldering condition inspecting apparatus defined by claim 7, wherein said first and second detecting means are connected to multiplication means, wherein a product of said effective voltage V and effective current I is obtained.

9. The soldering condition inspecting apparatus defined by claim 8, wherein said multiplication means is connected to latch means for temporarily holding said product V×I entered from said multiplication means.

10. The soldering condition inspecting apparatus defined by claim 9, wherein said product V×I is entered into said consumption energy calculating means.

11. The soldering condition inspecting apparatus defined by claim 4, further comprises judgement result memory means for memorizing the judging result of the soldering condition in said judging means.

12. The soldering condition inspecting apparatus defined by claim 11, further comprises control means for actuating said oscillation means in accordance with data stored in said judgement result memory means.

13. The soldering condition inspecting apparatus defined by claim 4, wherein said inspection tool is an inspection tool comprising a pin-like inspection piece fixed to a distal end of a horn.

14. The soldering condition inspecting apparatus defined by claim 13, wherein said horn is vibrated by said oscillation means, while a lower end of said inspection piece is depressed on the soldered portion of the inspected object.

15. A soldering condition inspecting method comprising steps of:

memorizing a reference waveform into a reference waveform memory means, said reference waveform representing a waveform obtainable when an inspection tool is vibrated by oscillation means under a predetermined reference condition;

calculating an actual energy consumed by said inspection tool based on a difference between said reference waveform and a waveform measured when said inspection tool is depressed against a soldered portion of an inspected object under vibration generated by said oscillation means; and making a judgement on whether the soldering condition of the soldered portion of the inspected object is acceptable by comparing the actual energy calculated in said calculating step with a target value.

16. The soldering condition inspecting method defined by claim 15, wherein said target value is an energy to be consumed by said inspection tool when the soldered portion of the inspected object is in a predetermined proper soldering condition, while said inspection tool is subjected to vibration generated by said oscillation means for a predetermined time.

\* \* \* \* \*